(12) United States Patent
Petersson et al.

(10) Patent No.: US 8,979,532 B2
(45) Date of Patent: Mar. 17, 2015

(54) DENTAL ATTACHMENT QUALITY TESTING DEVICE

(75) Inventors: Anders Petersson, Göteborg (SE); Callum Youngson, Heswall (GB)

(73) Assignee: Osstell AB, Gothenburg (SE)

( * ) Notice: Subject to any disclaimer, the term of this patent is extended or adjusted under 35 U.S.C. 154(b) by 373 days.

(21) Appl. No.: 12/980,717

(22) Filed: Dec. 29, 2010

(65) Prior Publication Data

US 2011/0200965 A1 Aug. 18, 2011

Related U.S. Application Data

(63) Continuation-in-part of application No. 12/393,931, filed on Feb. 26, 2009, now Pat. No. 8,391,958, which is a continuation-in-part of application No. 10/561,362, filed as application No. PCT/SE2004/000998 on Jun. 21, 2004, now abandoned.

(51) Int. Cl.
*A61C 13/12* (2006.01)
*A61C 19/04* (2006.01)
*A61C 8/00* (2006.01)

(52) U.S. Cl.
CPC .. *A61C 19/04* (2013.01); *A61C 8/00* (2013.01)
USPC ............................ 433/172; 600/437; 600/587

(58) Field of Classification Search
USPC .................................. 600/437, 587; 433/172
See application file for complete search history.

(56) References Cited

U.S. PATENT DOCUMENTS

| 3,292,426 | A | * | 12/1966 | McCann | .......................... 73/658 |
| 3,355,933 | A |   | 12/1967 | Rowe |   |
| 4,362,511 | A |   | 12/1982 | Jacklich |   |
| 4,511,330 | A |   | 4/1985 | Smiley et al. |   |
| 5,392,779 | A | * | 2/1995 | Meredith et al. | .............. 600/437 |
| 5,518,008 | A |   | 5/1996 | Cucchiaro et al. |   |
| 5,680,874 | A |   | 10/1997 | Takuno |   |
| 6,034,296 | A |   | 3/2000 | Elvin et al. |   |
| 6,161,046 | A | * | 12/2000 | Maniglia et al. | ................ 607/57 |
| 6,413,220 | B1 |   | 7/2002 | Rose |   |
| 6,583,630 | B2 |   | 6/2003 | Mendes et al. |   |
| 2002/0115944 | A1 | * | 8/2002 | Mendes et al. | ................ 600/594 |
| 2002/0143268 | A1 |   | 10/2002 | Meredith et al. |   |
| 2002/0177790 | A1 |   | 11/2002 | Meredith et al. |   |
| 2004/0204647 | A1 |   | 10/2004 | Grupp et al. |   |
| 2005/0026113 | A1 |   | 2/2005 | Chen et al. |   |

FOREIGN PATENT DOCUMENTS

| EP | 0602970 A2 | 6/1994 |
| EP | 0702942 A1 | 3/1996 |
| EP | 0853938 A1 | 7/1998 |
| JP | 08-089517 | 4/1996 |
| JP | 03-070752 | 3/2003 |

(Continued)

*Primary Examiner* — Max Hindenburg
*Assistant Examiner* — Renee Danega
(74) *Attorney, Agent, or Firm* — Pierce Atwood LLP; Kevin M. Farrell (57) ABSTRACT

The invention relates to a method and apparatus for testing attachment quality of a dental crown attached to a tooth and/or implant. The method comprises the steps of: detecting at least one resonance frequency of a member when it is in contact with said crown or a part attached to the crown; and interpreting the detected resonance frequency in terms of the degree of attachment of the crown to a tooth.

23 Claims, 5 Drawing Sheets

(56) References Cited

FOREIGN PATENT DOCUMENTS

| WO | 92/18053 | 10/1992 |
| WO | 96/05769 | 2/1996 |
| WO | 99/46603 | 9/1999 |
| WO | 01/19248 | 3/2001 |
| WO | 01/22880 | 4/2001 |
| WO | 2004110272 A1 | 12/2004 |

* cited by examiner

DENTAL ATTACHMENT QUALITY TESTING DEVICE

RELATED APPLICATIONS

This present application claims priority to U.S. patent application Ser. No. 12/393,931, filed on Feb. 26, 2009, which claims priority to U.S. patent application Ser. No. 10/561, 362, filed on Mar. 8, 2007, which claims priority to PCT/SE04/00998, filed on Jun. 21, 2004, which claims priority to Swedish Patent Application Serial No. SE 0301825-6, filed on Jun. 19, 2003.

FIELD OF THE INVENTION

The present invention relates to a method and apparatus for testing attachment quality a crown especially a crown of a dental bridge attached to a tooth or an implant of a human or an animal subject.

BACKGROUND

Dental bridges are tooth restorations that can be used to replace missing teeth. They are an excellent alternative to dentures and dental implants; they provide more stability than dentures and the procedure is less invasive then the placement of dental implants. Dental bridges are one method used by dentists to till a gap created by a missing tooth (or teeth). Depending on the dental bridge type, the attachment procedure and cost varies.

Figure 1:
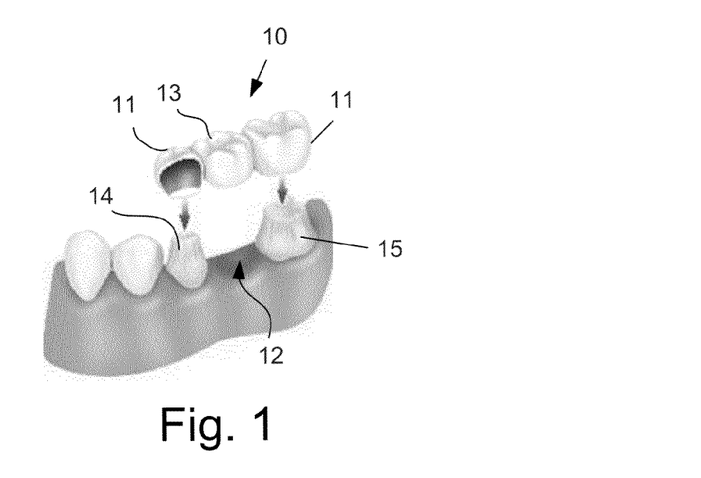
FIG. 1 is a schematic view of a dental bridge.

Referring now to FIG. 1, normally a dental bridge 10 is made up of two dental crowns 11 for the teeth on either side of the gap 12 and a false or replacement tooth 13 in between. Natural teeth 14 and 15, dental implants or a combination of natural teeth and dental implants can be used to support the bridge 10.

During the first treatment, the dentist may sculpt down the teeth on either side of the gap left by the missing tooth. Once the teeth have been sufficiently prepped, a mold, or impression, is taken and sent to a dental laboratory where specialists can custom make your bridge and the crown restorations. Finally, temporary crowns and a bridge will be placed to protect the patients' teeth and gums from further damage.

Most patients will return to the dentist about a week after their initial appointment to have the permanent restorations placed. The dentist will use cement or a bonding solution to hold the crowns and bridge in place and then polish the cusps of the restorations to provide you with a comfortable bite.

Although the dental bridge treatment is an effective solution for patients with some missing teeth, there are some risks and limitations associated with the treatment.

One major risk is the attachment of the crowns to the surrounding teeth. If there is a loose contact between the crown and the teeth, the risk for caries increases. The most common reason for fixed bridge replacement is caries, or decay of the underlying tooth structure. Once either abutment tooth of a bridge develops caries (decay) the entire bridge, which is at least three crowns, must be replaced. Often the abutment tooth will also need more treatment such as a pulp cap, core build up, crown lengthening or root canal therapy.

SUMMARY

Thus, there is need to detect whether there is a problem in the attachment between the crown(s), especially dental bridge crowns and a tooth and/or an implant.

Thus, there is a need for a means of clinically observing the quality of the attachment between the crown and the tooth surface. A non-destructive test would help to reduce failures of this type, and would also enable periodic tests to be carried out on the bridge attachments, which are in use to ensure that they are still satisfactory.

It is therefore an object of the present invention to provide a non-destructive test which is capable of giving a reliable indication of the quality and/or extent of the attachment between a crown and the tooth to which it is attached.

Accordingly there is provided a method of testing attachment quality of a dental crown attached to a tooth, an implant, or both. The method comprises: detecting at least one resonance frequency of a member when it is in contact with said crown or a part attached to the crown; and interpreting the detected resonance frequency based on degree of attachment of the crown to a tooth, an implant, or both. The method may include the step of releasably attaching the member to the crown or a part attached to it. The member may comprise a cantilever beam. The beam is attached to said crown or part attached to the crown trough a threaded bore. The beam may also be attached to said crown or part attached to the crown by means of an adhesive agent. The beam may be incorporated in said crown or the part attached to it.

The method may include the step of comparing the detected resonance frequency with one or more values for the resonance frequencies of the same or similar member from an earlier measurement. The method may include the steps of exciting the member with an AC signal, detecting the response of the member to the AC signal, and varying the frequency of the AC signal until the detected response of the member is at a maximum. The method may include deriving an output which is the ratio of the voltage of the response signal to that of the excitation signal. The method could also include performing a pulse-excitation of the member and detecting the response and performing a frequency analysis of the response signal. Preferably, the measurement is contactless.

The invention also relates to a dental crown attachment quality testing apparatus. The apparatus comprises a detector for detecting at least one resonance frequency of a member when it is attached to the dental crown. The detector for detecting at least one resonance frequency of the member may comprise means for exciting the member with an AC signal, and a transducer for detecting the response of the member to the AC signal, the arrangement being such that the frequency of the AC signal is varied, and the transducer detects when the response of the member is at a maximum. The excitation means and/or detector may comprise a piezoelectric element, the piezoelectric element comprising the excitation means being driven by a variable frequency oscillator. The member comprises a detectable part and that said detector part comprises a detector for contactless detection of said detectable part.

According to one embodiment, the member may comprise a magnetic portion and the detector may comprise a coil.

According to one embodiment, the member may comprise a marker and the detector comprises an illumination detector.

According to one embodiment, the member may consist of a ferromagnetic material and the detector may comprise a coil for detecting disturbances in an external magnetic field.

The apparatus may further comprise an amplifier, a processor, and a data store. The signal processing unit is further configured to vary a frequency output of an oscillator, and stores the results in said data store. At least one coil may be configured to output magnetic pulses to a member attached to said member and detect responses corresponding to said magnetic pulses from said member.

Other aspects and advantages of the current invention will become apparent from the following detailed description, taken in conjunction with the accompanying drawings, illustrating the principles of the invention by way of example only.

BRIEF DESCRIPTION OF THE DRAWINGS

The invention will now be further described, by way of example only, with reference the accompanying drawings, in which.

DETAILED DESCRIPTION OF ILLUSTRATIVE EMBODIMENTS

Figure 2:
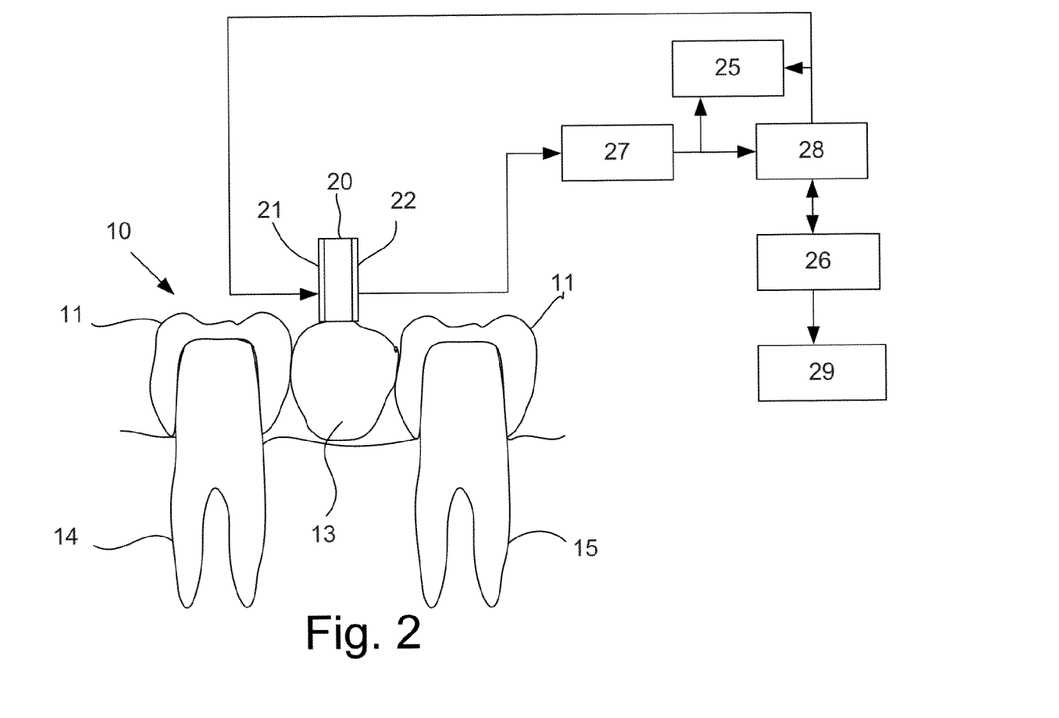
FIG. 2 is a schematic diagram of a second embodiment of apparatus according to the invention.

Referring to FIG. 2, the apparatus comprises a member in the form of a cantilever beam 20 attached by means of, e.g. a threaded section to an fixture in a suitable position on the bridge 10 (in this case the false tooth) or adhesive. The bridge may be any one of a number of known types. Two transducers, such as piezoelectric elements or strain gauges 21 and 22, are attached, for example bonded, to opposite sides of the beam 20, gauge 21 being an exciter gauge and gauge 22 a receiver gauge.

The exciter gauge 21 may be driven by a variable frequency oscillator, signals from which, for example in the form of a sinusoidal excitation voltage, are fed to the gauge 21 via an amplifier. The oscillator and amplifier may be incorporated in a frequency response analyzer 28.

Signals detected by the receiver gauge 22 are amplified by a charge amplifier 27 and applied as an input to the analyzer 28. The output from the analyzer, which represents the ratio of the response voltage to the excitation voltage, is fed to a processor such as a microprocessor 26, which is used to vary the frequency output of the oscillator of the analyzer 28, and store the results in a data store 29. The results may be printed out, and/or displayed on an oscilloscope 25, and/or an AC voltmeter or the like.

In use the beam 20 is secured, i.e. screwed, to the bridge 10. Constant amplitude, for example 1 volt, AC excitation signals are then applied to the beam 20 via the gauge 21. The frequency of the AC excitation signals is varied until the amplitude of the signal displayed on the oscilloscope 25 is at a maximum. The resonance frequency is the frequency at which the amplitude of the ratio of the response voltage to the excitation voltage is a maximum.

Figure 6:
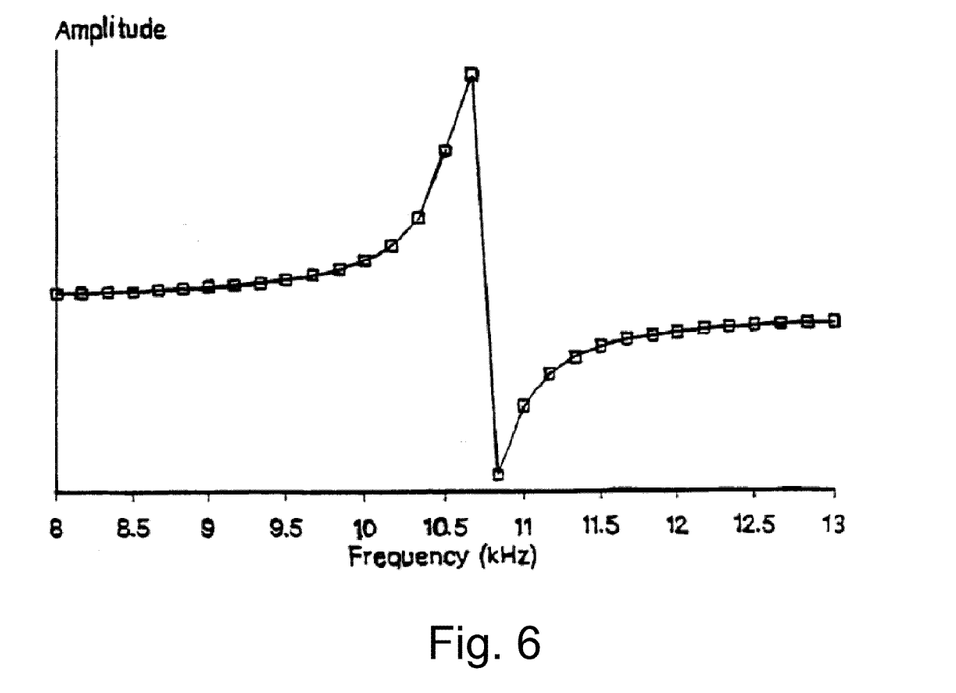
FIG. 6 is a diagram from a coarse sweep used to obtain resonance frequencies.

FIG. 6 shows the data from a coarse sweep which is used to obtain the resonance frequency roughly. A finer sweep around this region is then used to identify this frequency, typically the first or fundamental frequency, more accurately. This frequency is noted, and compared, for example, with the data for other bridges/crowns at similar stages of bonding.

Figure 7:
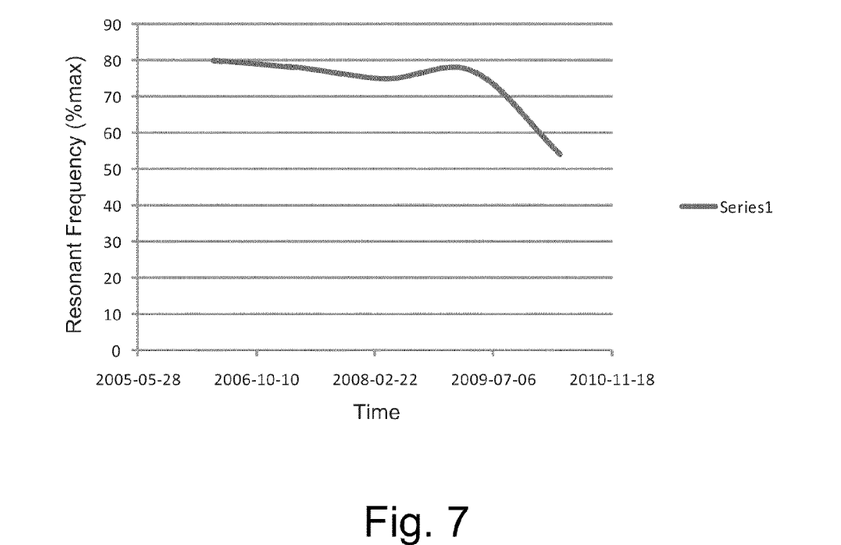
FIG. 7 is a schematic diagram illustrating the resonance frequency varying with time for a particular bridge.

It is expected that for a particular bridge attachment, the resonance frequency will vary with time as depicted in FIG. 7. Thus by comparing the detected resonance frequency with previously compiled data for similar earlier measurements, an indication of the degree of attachment of the crown to the tooth can be obtained.

The technique, which is based on detection and comparison of resonance frequency shifts, rather than amplitude changes, is effective to determine the quality of the attachment between the crown(s) and the tooth (teeth) as a function of its stiffness.

The beam 20 as shown in FIG. 2 may preferably be of metal such as aluminum, stainless steel or titanium, is dimensioned so as to provide a resonant frequency range of the system of the order of 1 to 20 kHz, more specifically 5 to 15 kHz, and preferably in the region of about 10 kHz.

It will be understood that various modifications may be made without departing from the scope of the present invention as defined in the appended claims.

For example, an additional pair of excitation/detection transducers or gauges may be mounted on the sides of the beam at 90° to the transducers or gauges 21 and 22 shown, so as to provide readings at right angles to the latter transducers, without the necessity of re-orienting the beam on the bridge. Additionally, or alternatively, the beam and/or transducer system could be adapted to turn relative to the dental bridge or crown.

The transducers or gauges, and optionally also the beam may be coated, for example with an air dry acrylic material, to protect the transducers during sterilization of the apparatus. The electrical connections or wires connected to the transducers are arranged or adapted to minimize their damping effect on the resonant structure. The member may take a form other than a cantilever beam, and/or the piezoelectric transducers could be replaced by other receiver/transmitter elements, for example employing sonic resonance. The beam, instead of being basically straight, could be generally U-shaped, and connected to the bridge or crown by its base. The transducers or equivalent could be mounted on the same or opposite limbs.

According to a second aspect of the invention, the measurement is carried out contactless.

Figure 3:
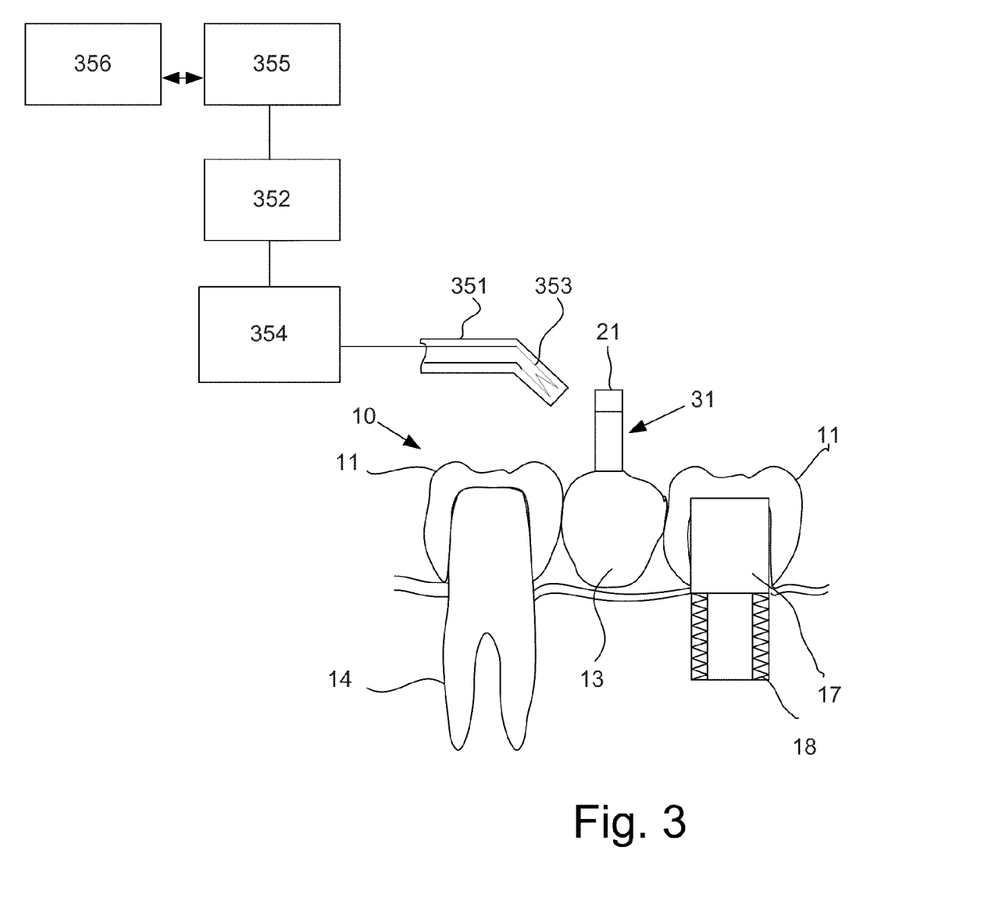
FIG. 3 is a schematic diagram of a second embodiment of apparatus according to the invention.

Referring to FIG. 3, the system includes a member 30 in the form of a cantilever beam attached to the bridge 10. The member 30 is provided with a magnetic member 31. The magnetic member 31 can be provided at one end of the beam 30, e.g. the free end or integrated inside the beam.

The second part of the system comprises the testing apparatus 35, including a probe 351 and a response analyzer unit 352. The probe 351 comprises a coil 353 for detecting oscillations of the magnetic member 31.

In this case one of the crowns 11 is attached to an implant 17 instead of a tooth. The implant is anchored to a bone by means of a screw portion 18.

To generate oscillations in the beam, it must be excited. This can be done manually or by means of an electrical exciter, through application of a force F on the beam.

Signals detected by the probe 350 are amplified by an amplifier 354 and applied as an input to the analyser. The output from the analyser, which represents the ratio of the response voltage to the excitation, is fed to a processor such as a microprocessor 355, which is used to vary the frequency output of the oscillator of the analyser, and store the results in a data store 356. The results can be printed out and/or displayed on a display or the like.

Figure 4:
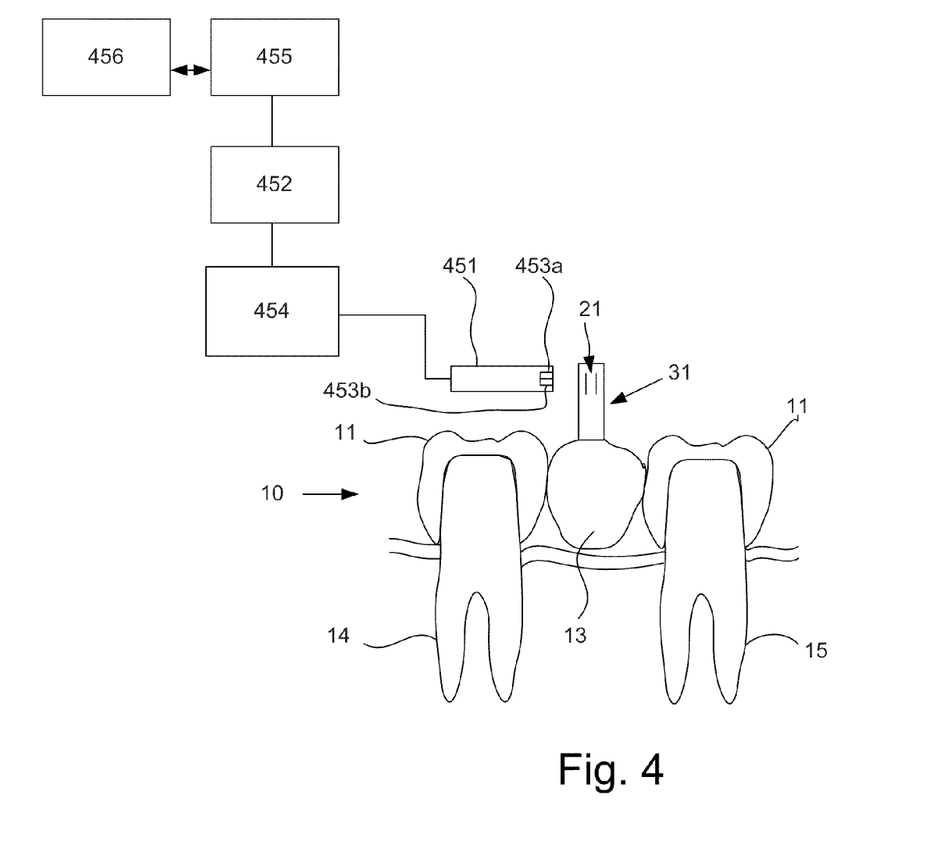
FIG. 4 is a schematic diagram of third embodiment of apparatus according to the invention.

Referring now to FIG. 4, illustrating a third embodiment of the invention, the first part of the arrangement according to the invention comprises, a member in the form of a cantilever beam 31 as in the earlier embodiment attached to the dental bridge 10. The beam 31 in this case is provided with markings 42, such as lines, arranged at one end of the beam 21.

The second part of the arrangement comprises the testing apparatus 450, including a probe 451 and a response analyzer unit 452. The probe 450 comprises a light source 453a, preferably but not exclusively a laser, and a light detector 453b for detecting reflections from the beam and thus oscillations of the beam. The light source is preferably Laser diode. The beam is provided with one or several markers, such as darker (or lighter) sections, which effect the reflection of the light.

The beam is excited manually or e.g. means of an electrical exciter, by applying e force on the beam.

The light source on the tip of the probe illuminates the beam and the light detector 453b detects the reflected light. The detected light signal is converted to an electrical signal by the detector, and signals detected by the probe 451 are amplified by an amplifier 454 and applied as an input to the analyser. The output from the analyser, which represents the ratio of the response voltage to the excitation, is fed to a processor such as a microprocessor 455, which is used to vary the frequency output of the oscillator of the analyser, and store the results in a data store 456. The results can be printed out, and/or displayed on a display or the like.

In use the beam 31 is secured to the dental bridge 10. Preferably, but not necessarily, the beam according to the invention is disposable, which means that it can be detached and disposed, providing a hygienic testing arrangement.

Figure 8:
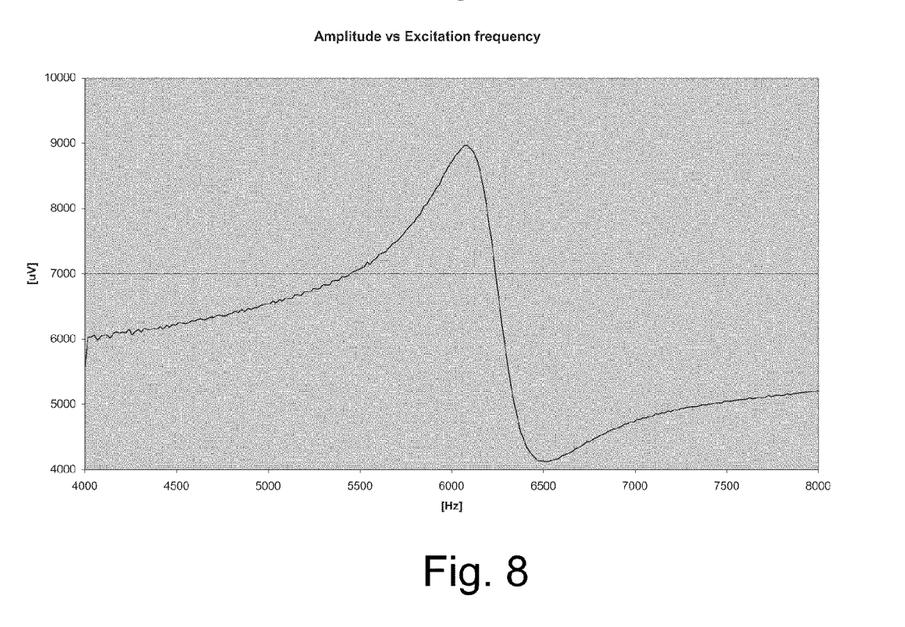
FIG. 8 is a diagram illustrating the data from a sweep used to obtain the resonance frequency the apparatus of FIG. 3.

FIG. 8 shows the data from a coarse sweep, which is used to obtain the resonance frequency roughly in the apparatus of FIG. 3. A finer sweep around this region is then used to identify this frequency, typically the first or fundamental frequency, more accurately. This frequency is noted, and compared, for example, with the data for an earlier measurement (e.g., when the bridge was mounted).

It is expected that for a particular bridge, the resonance frequency will vary with the degree of attachment of the crowns to the teeth. Thus, by comparing the detected resonance frequency with previously compiled data for same bridge, an indication of the degree of attachment of the bridge can be obtained.

The technique, which is based on detection and comparison of resonance frequency shifts, rather than amplitude changes, is effective to determine the quality of the attachment.

The beam may preferably be of a metallic material, for example titanium or aluminium, is dimensioned so as to provide a resonant frequency range of the system (placed bridge and beam) of the order of 1 to 20 kHz, more specifically 1 to 10 kHz, and preferably in the region of about 8 KHz. For example, in the embodiment of FIGS. 2 and 3, the upright beam can be approximately 1 cm high.

In yet another embodiment the beam may be made of a ferromagnetic material and can be brought into excitation by means of an external magnetic field generated by a field generator. The field generator can be a permanent magnet for generating a DC field or a coil for generating an AC filed. The probe may also be externally arranged.

The magnet attached to a smart peg (beam) may be excited with magnetic pulses. After each pulse, the alternating magnetic field that is the result of the self-vibrating peg is picked up by the electric coil in the measurement probe. The magnetic pulses may be generated by another coil in the same probe (or an additional probe).

The metal pegs have a simplified mechanical design compared to the transducers, and do not require individual calibration. It is not possible to store any calibration parameters in them since they are not electrically connected to the instrument. Instead, the individual differences between pegs are reduced to a minimum by a carefully controlled manufacturing process.

The pegs also have a simpler mechanical behavior when they are vibrating at their resonance frequency. They are more sensitive and have a predictable behavior down to very low attachment stability.

A measurement may consist of a number of pulses, e.g. 4 or 30 pulses. In the case of 30 pulses, these pulses cover the frequency spectrum from 1 to 10 kHz. Since the pulses are more narrow-band, the 30 pulses contain more energy. This makes the responding signal stronger, and the signal to noise ratio is improved, making the measuring device of the invention less sensitive to surrounding electromagnetic noise. It is recognized by a skilled person that the number of pulses are not limited to 4 or 30.

Figure 5:
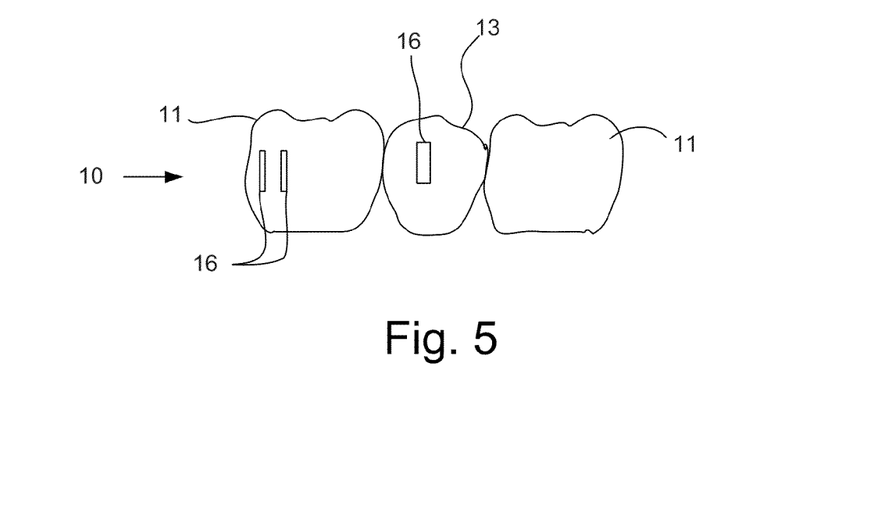
FIG. 5 is a schematic diagram of a dental bridge according to one embodiment of according to the invention.

An embodiment of a dental bridge 10 is illustrated in FIG. 5. In the embodiment, detectable portions such as magnetic or optical portions 16 are incorporated in the crowns 11 or the false tooth 13. This embodiment allows using same measuring points.

It will be understood that various modifications may be made without departing from the scope of the present invention as defined in the appended claims.

The transducers or gauges, and optionally also the beam may be coated, for example with an air-dry acrylic material, to protect the transducers during sterilization of the apparatus. The member may take a form other than a cantilever beam. The beam, instead of being basically straight, could be generally U-shaped, and connected to the bridge by its base. Moreover, alternative detectors, such UV, sound, and the like can also be used.

The invention is not limited to bridges and can be applied to crowns or other arrangements to be attached to a tooth.

Comprise, include, and/or plural forms of each are open ended and include the listed parts and can include additional parts that are not listed. And/or is open ended and includes one or more of the listed parts and combinations of the listed parts.

One skilled in the an will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

The invention claimed is:

1. A method of testing quality of attachment of a dental crown attached onto a surface of a tooth or an implant, the method comprising the steps of:
    placing a member in mechanical communication with a dental crown;
    exciting the member to physically oscillate by an external magnetic field;
    contactlessly detecting magnetic field interference of said member to detect at least one resonance frequency of the member during excitation when it is in contact with said dental crown or a part attached to the dental crown; and
    interpreting, by an analyzer, the detected at least one resonance frequency, wherein an output of the analyzer represents a ratio of a response voltage to the excitation to provide a degree of attachment of attachment of the dental crown onto said surface of a tooth or implant.

2. The method according to claim 1, wherein placing the member in mechanical communication with the dental crown comprises the step of releasably attaching the member to the dental crown or part attached to the dental crown.

3. The method according to claim 1, wherein the member comprises a cantilever beam.

4. The method according to claim 3, wherein the beam is attached to said dental crown or the part attached to the dental crown through a threaded bore.

5. The method according to claim 3, wherein the beam is attached to said dental crown or the part attached to the dental crown by means of an adhesive agent.

6. The method according to claim 3, wherein the beam is incorporated in said dental crown or the part attached to the dental crown.

7. The method according to claim 1, comprising the step of comparing the detected resonance frequency with one or more values for resonance frequencies of the same or similar member in communication with the same crown from an earlier measurement.

8. The method according to claim 1, comprising the step of performing a pulse-excitation of the member and detecting the response and performing a frequency analysis of the response signal.

9. The method according to claim 1, wherein said member comprises a magnetic part.

10. The method according to claim 9, wherein contactlessly detecting the at least one resonance frequency of the member during excitation comprises detecting physical oscillations in the magnetic part of the member by a probe including a coil.

11. The method according to claim 10, wherein said magnetic part is formed from a ferromagnetic material.

12. The method according to claim 10, wherein said resonance frequency is detected by disturbance of the external magnetic field by the magnetic part of the member.

13. The method according to claim 1, further comprising the step of comparing the detected resonance frequency with one or more values for resonance frequencies of the same or similar member in communication with a different crown from an earlier measurement.

14. A dental crown attachment quality testing apparatus, the apparatus comprising a detector adapted to contactlessly detect interferences of a magnetic field of a member when attached to said dental crown, generated by an exciter exciting by means of an external magnetic field to said dental crown the member in mechanical communication with the dental crown to physically oscillate, the detector being further configured for detecting at least one resonance frequency of the physical oscillations of the member when it is attached to the dental crown, when said dental crown is attached to a surface of a tooth or implant and for generating an output wherein the output represents a ratio of response voltage to the excitation to provide a degree of attachment quality of the dental crown onto said surface of said tooth or implant.

15. The apparatus according to claim 14, further comprising an amplifier, a processor, and a data store.

16. The apparatus according to claim 15, wherein said signal processing unit is further configured to vary a frequency output of an oscillator, and to store the results in said data store.

17. The apparatus according to claim 16, comprising at least one coil configured to output magnetic pulses to said member attached to the dental crown or a part attached to the dental crown and detect responses corresponding to said magnetic pulses from said member.

18. The apparatus according to claim 14, wherein the member comprises a cantilever beam.

19. The apparatus according to claim 18, wherein the member is further adapted to resonate at a frequency within the range of about 1 to 20 kHz.

20. The apparatus according to claim 14, wherein said member is disposable.

21. The apparatus according to claim 14, wherein said member comprises a magnetic portion.

22. The apparatus according to claim 21, wherein said magnetic portion consists of a ferromagnetic material.

23. The apparatus according to claim 22, wherein said detector comprises a coil for detecting disturbances in an external magnetic field.

* * * * *

UNITED STATES PATENT AND TRADEMARK OFFICE
CERTIFICATE OF CORRECTION

| | | |
|---|---|---|
| PATENT NO. | : 8,979,532 B2 | Page 1 of 1 |
| APPLICATION NO. | : 12/980717 | |
| DATED | : March 17, 2015 | |
| INVENTOR(S) | : Anders Petersson and Callum Youngson | |

It is certified that error appears in the above-identified patent and that said Letters Patent is hereby corrected as shown below:

On the Title Page please add the following after the Related U.S. Application Data section:

--(30) Foreign Application Priority Data

June 19, 2003 (SE) 0301825-6--.

Signed and Sealed this
Fifteenth Day of September, 2015

Michelle K. Lee
*Director of the United States Patent and Trademark Office*